United States Patent [19]

Kant et al.

[11] Patent Number: 5,043,439

[45] Date of Patent: Aug. 27, 1991

[54] PROCESS FOR PRODUCTION OF CEPHALOSPORINS

[75] Inventors: Joydeep Kant, Liverpool; Chester Sapino, Jr., E. Syracuse, both of N.Y.

[73] Assignee: Bristol-Myers Squibb Company, New York, N.Y.

[21] Appl. No.: 490,213

[22] Filed: Mar. 8, 1990

[51] Int. Cl.$^5$ ............................................. C07D 501/04
[52] U.S. Cl. ................................. 540/215; 540/222; 540/228; 540/229; 540/230
[58] Field of Search ............... 540/215, 222, 228, 229, 540/230

[56] References Cited

U.S. PATENT DOCUMENTS

| | | | |
|---|---|---|---|
| 3,985,737 | 10/1976 | Spitzer | 540/227 |
| 4,847,373 | 7/1989 | Baker et al. | 540/215 |
| 4,855,418 | 8/1989 | Cook et al. | 540/222 |
| 4,870,168 | 9/1989 | Baker et al. | 540/227 |

FOREIGN PATENT DOCUMENTS 1444224 7/1976 United Kingdom .

OTHER PUBLICATIONS

D. O. Spry et al., *Heterocycles*, 23, No. 8, 1985; pp. 1901–1905.

B. H. Lipshutz et al., *J. Am. Chem. Soc.* 1989; 111, 1351–1358.

B. H. Lipshutz et al., *Synthesis* Apr. 1987—pp. 325–341.

*Primary Examiner*—Mukund J. Shah
*Assistant Examiner*—Jyothsna Venkat
*Attorney, Agent, or Firm*—Mollie M. Yang

[57] ABSTRACT

Cephalosporin intermediates having a replacable organosulfonyloxy or heterocyclothio group in the 3-position undergo a carbon alkylation process with organocopper reagents to provide 3-hydrocarbon substituted cephalosporin antibiotics.

11 Claims, No Drawings

PROCESS FOR PRODUCTION OF CEPHALOSPORINS

FIELD OF THE INVENTION

This invention provides a process for synthesizing cephalosporin antibiotics of the structural type characterized by an alkyl, alkenyl, or araryl group in the 3-position. The process involves the carbon alkylation of certain 3-functionalized cephalosporin intermediates mediated by an organocopper reagent whereby the organic group is transferred from the reagent to the cephalosporin.

DESCRIPTION OF THE PRIOR ART

Dimethyllithium cuprate has been used to alkylate a 3-bromomethylcephalosporin in tetrahydrofuran solution at $-70°$ C. B. Laundon. et al., British Patent Specification 1.444.224 published July 28, 1976.

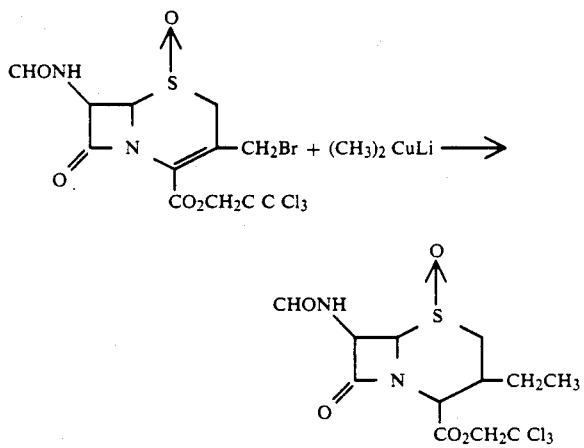

3-Halomethylcephems have been alkylated in a similar fashion With vinylstannanes under the influence of palladium catalysts. Refer to Baker. et al.. U.S. Pat. No. 4,847,373 patented July 11, 1989.

Similarly. 3-halocephems have been alkylated with the above organocopper reagent by D.O. Spry. et al., Heterocycles, 23, No. 8, 1985, pp. 1901–1905.

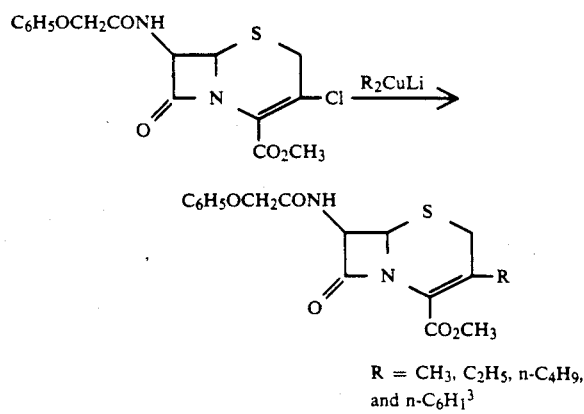

$R = CH_3, C_2H_5, n-C_4H_9,$
and $n-C_6H_{13}$

The corresponding 3-phenylthio cephalosporin was alkylated by Spry, et al., in the same fashion.

The role of boron trifluoride etherate in facilitating the conjugate addition of dialkyllithium cuprate reagents to $_{60}, _{62}$-unsaturated ketones has been reported upon by B. H. Lipshutz, et al.. J. Am. Chem Soc. 1989, 111. 1351–1358. A review article covering higher order mixed cuprates in organic synthesis by B. H. Lipshutz has been published, "Synthesis" Apr., 1987 - pp. 325–341.

Baker. et al., U.S. Pat. No. 4,870,168, patented Sept. 26, 1989 describe the carbon alkylation of the cephalosporin 3-position by reaction of a 3-trifluoromethanesulfonyloxycephem with an alkyltin reagent in the presence of a palladium catalyst.

The 3-trifluoromethanesulfonyloxycephem referred to in Baker, et al., U.S. Pat. No. 4,870,168 serves as a starting material for the present process. The corresponding p-toluenesulfonyloxy and p-nitrobenzenesulfonyloxy cephems have been described by W. A. Spitzer, in U.S. Pat. No. 3,985,737, patented Oct. 12, 1976 as antibiotic products also may also serve as starting materials for the present process.

SUMMARY OF THE INVENTION

The process of the present invention may be illustrated by the following reaction diagram.

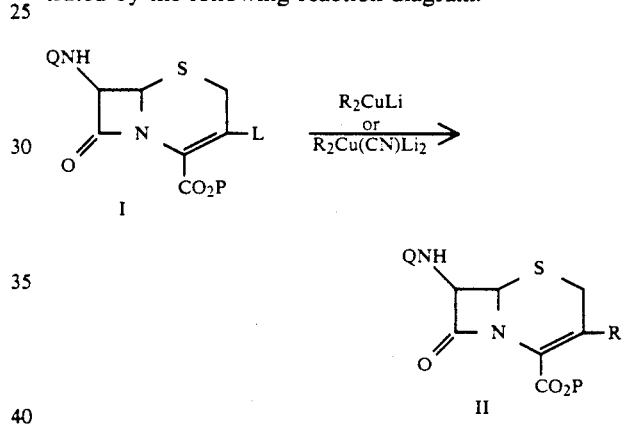

The symbols Q, P, and R will be described more fully hereinafter. L is a leaving group selected from trifluoromethanesulfonyloxy, p-toluenesulfonyloxy, p-nitrobenzenesulfonyloxy, 1-methyl-tetrazol-5-ylthio, and benzthiazol-2-ylthio. The reaction is carried out by contacting the cephalosporin starting materials, I, with the organocopper reagent, $R_2CuLi$ or $R_2Cu(CN)Li_2$, in a reaction inert aprotic solvent within the temperature range of $-78°$ C. to $0°$ C. At least a stoichiometric amount of the organocopper reagent is used, but preferably from 2 to 3 times the stoichiometric amount is employed. The reaction is carried out protected from atomospheric oxygen, carbon dioxide and moisture. Anhydrous conditions throughout the reaction period of from 1 to 5 hrs. are maintained.

The product is recovered by quenching the reaction mixture with multiple volumes of water, or preferably saturated ammonium chloride solution, and extracting with a water immiscible organic solvent such as dichloromethane or other solvent according to the skill of the art. Purification is achieved by recrystallization or flash chromatography.

The products of Formula II include both known and novel cephalosporin antibiotic compounds. Examples of known antibiotic products that may be produced by the present process include the following:

Cephalexin
(U.S. Pat. No. 3,507,861)

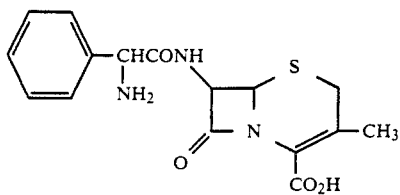

Cefadroxil
(U.S. Pat. No. Re. 29,164)

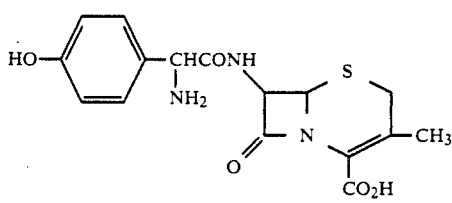

Cephradine
(U.S. Pat. No. 3,485,819)

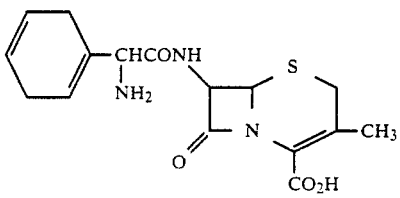

Cefprozil
(U.S. Pat. No. 4,520,022)

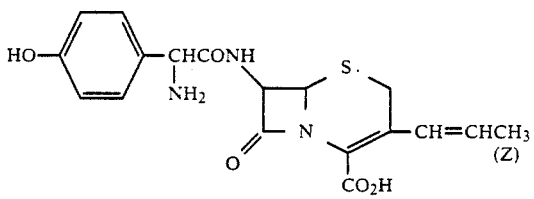

BMY-28271
(U.S. Pat. No. 4,708,955)

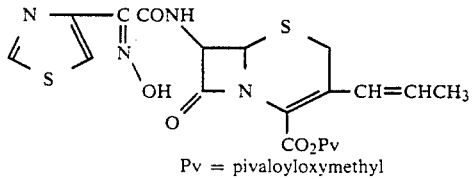

Pv = pivaloyloxymethyl

DETAILED DESCRIPTION OF THE INVENTION

Q in Formulas I and II above is hydrogen, an amino protecting group of the sort conventionally used in cephalosporin processes, or the acyl group of a known 7-acylaminocephalosporin antibiotic.

"An amino protecting group" of the sort conventionally used in cephalosporin synthesis includes, but is not limited to, lower alkanoyl or substituted lower alkanoyl, e.g. formyl, acetyl, chloroacetyl, and trifluoroacetyl: aroyl or substituted aroyl, e.g. benzoyl, 4-methoxybenzoyl, and 4-nitrobenzoyl: aralkyl, substituted aralkyl, aralkylidene, or substituted aralkylidene, e.g. benzyl, diphenylmethyl, trityl, nitrobenzyl, methoxybenzyl, and benzylidene; halogenated alkyl, e.g. trichloromethyl, trichloroethyl, and trifluoromethyl; alkoxycarbonyl or substituted alkoxycarbonyl, e.g. methoxycarbonyl, ethoxycarbonyl, t-butoxycarbonyl, cyclohexyloxycarbonyl, and trichloroethoxycarbonyl; aralkoxycarbonyl or substituted aralkoxycarbonyl, e.g. benzyloxycarbonyl, methoxybenzyloxycarbonyl, and nitrobenzyloxycarbonyl; an unsubstituted or substituted trialkylsilyloxycarbonyl or triarylsilyloxycarbonyl; and trialkylsilyl or triarylsilyl groups, e.g. trimethylsilyl and t-butyldimethylsilyl. Amino protecting groups and their use are described in the textbook "Protective Groups in Organic Synthesis" by Theodora W. Greene, John Wiley & Sons, New York 1981 Chapter 5.

"Acyl group of a known 7-acylaminocephalosporin antibiotic" refers to the substituent of the 7-amino group of a known cephalosporin antibiotic and may be represented by the formula R—C(0)—. Examples of R include, but are not limited to,

(a)

wherein G may be substituted or unsubstituted aryl, heterocyclic, or cyclohexadienyl group, e.g. phenyl, thienyl, thiazolyl, thiadiazolyl, imidazolyl, pyridyl, tetrazolyl, 1,4-cyclohexadienyl, and furyl; the substituents for the groups may be 1 to 3 of the same or different groups selected from halogen, hydroxy, amino, alkoxy, alkylamino, dialkylamino, alkanoyloxy, carboxy, nitro, cyano, and alkoxycarbonyl; G, may be hydrogen, hydroxy, amino, monoalkylamino, dialkylamino, alkanoylamino, alkanoyloxy, carboxy, and sulfo;

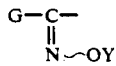
(b)

wherein G has the same meaning given above, and Y is hydrogen, $C_{1-6}$alkyl, or $C_{1-6}$alkanoyl;

(c) G—B—CH$_2$—wherein G has the same meaning given above, and B is oxygen or sulfur; and

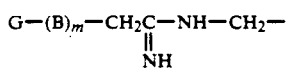
(d)

where G. and B have the meanings given above, and m is 0 or 1.

Some specific examples of "acyl group of a known 7-acylaminocephalosporin antibiotic" include 2-amino-2-phenylacetyl, 2-amino-2-(4-hydroxy)phenylacetyl, 2-thienylacetyl, phenylacetyl. 2-hydroxy-2-phenylacetyl, 2-acetoxy-2-phenylacetyl. 1-tetrazolylacetyl. [(2-amino-4-thiazolyl)(methoxyimino)]acetyl. phenoxyacetyl, and [(2-furanyl)(methoxyimino)]acetyl.

The skilled chemist will appreciate that when applying the present process to the preparation of end-products of Formula II wherein Q is the acyl group of a cephalosporin antibiotic which contains a functional group such as hydroxy, amino, or carboxy which may be reactive under the conditions of the present process that an appropriate protecting group rendering said functional group non-reactive under the conditions of the present process will be employed. Guidance for selecting and using such protecting group is given in the above cited Greene textbook. Another expedient is to employ a starting material I having a "Q" group which is stable under the process conditions, and to then replace that Q with the desired end-product Q group in subsequent synthetic steps.

The group L is defined above. It should be appreciated, however, that other equivalent leaving groups can be identified by the skilled chemist with a minimum of experimentation. For instance, a few milligrams of a starting material of Formula I wherein L is a putative leaving group other than those named can be subjected to the process conditions on a test tube scale, and the occurance of L-replacement determined spectrometrically by NMR or other means.

P in Formulas I and II is hydrogen a carboxy protecting group conventionally used in cephalosporin synthesis, a cation. or a physiologically hydrolyzable ester group. "A carboxy protecting group" may be any that is readily replaced with hydrogen under conditions which do not affect other functional groups in the molecule. Such groups and conditions suitable for their formation and replacement are described in the above cited Greene textbook pp. 151-192. Examples of carboxy protecting groups in cephalosporin synthesis include, but are not limited to, optionally substituted lower alkyl such as methyl, ethyl, trichloromethyl, trichloroethyl, tertiary butyl, methoxymethyl, methoxyethyl; acetoxymethyl, acetoxyethyl, and methanesulfonylmethyl; optionally substituted aralkyl such as diphenylmethyl, trityl, monomethoxytrityl, benzyl, 4methoxybenzyl, and 4-nitrobenzyl; silyl groups such as trimethylsilyl and t-butyldimethylsilyl; lower alkenyl such as vinyl and allyl; and aryl such as phenyl, tolyl; etc.

"A cation" includes, but is not limited to, alkali metal, e.g. sodium, lithium, and potassium, alkaline earth metal, e.g. calcium and magnesium; ammonium; and alkylammonium, e.g. trimethylamine and triethylamine.

"A physiologically hydrolyzable ester" includes, but is not limited to, a lower alkoxycarbonyloxyalkyl group, e.g. ethoxycarbonyloxyethyl; a lower alkylcarbonyloxyalkyl group, e.g. acetoxymethyl and pivaloyloxymethyl; and an (2-oxo-1,3-dioxolene4-yl)methyl group, e.g. (4-methyl-2-oxo-1,3-dioxol-5-yl)methyl. Such esters are hydrolyzable by the blood or digestive enzymes following injection or ingestion into a mammal.

R in the organocopper reagent, and in the Formula II product, is the desired cephalosporin end-product 3-substituent which is introduced by the present process. It is desirably $C_{1-6}$ alkyl, $C_{2-6}$alkenyl, $C_{4-6}$alkynyl, $C_{2-6}$alkadienyl, any of which groups may be straight-chained or branched-chained. $C_{6-1}$aryl (e.g. phenyl, naphthyl), or substituted $C_{6-1}$aryl bearing from 1 to 3 varied or similar substituents selected from $C_{1-3}$alkyl. hydroxy, $C_{1-3}$alkoxy, halo, amino, $C_{1-3}$alkylamino. diC$_{1-3}$alkylamino. nitro, carboxy, $C_{1-3}$alkoxycarbonyl, or cyano.

It will be appreciated that the above listings serve only to illustrate what the various terms may include; these listings are by no means exhaustive and are not to be construed as limiting.

A preferred embodiment of the process provides compounds wherein R is (Z)-prop-1-en-1-yl including cefprozil.

Another preferred embodiment of the process provides compounds wherein Q is an amine protecting group. More preferably, the protecting group t-butoxycarbonyl or benzyloxycarbonyl.

Another preferred embodiment of the process provides compounds wherein Q is 2-amino-2-phenylacetyl. 2-amino-2-(4hydroxy)phenylacetyl, 2-thienylacetyl, phenylacetyl, 2-hydroxy-2phenylacetyl, 2-acetoxy-2-phenylacetyl, 1-tetrazolylacetyl, [(2-amino-4-thiazolyl)-(methoxyimino)]acetyl, phenoxyacetyl, or [(2furanyl)-(methoxyimino)]acetyl. More preferably Q is selected from 2-amino-2-phenylacetyl, 2-amino-2-(4-hydroxy)-phenylacetyl, phenylacetyl, and phenoxyacetyl.

Another preferred embodiment of the process provides compounds wherein P is a carboxy protecting group selected from benzyl, diphenylmethyl, trityl, 4-nitrobenzyl, and 4-methoxybenzyl. More preferably P is selected from diphenylmethyl and 4-methoxybenzyl.

Compounds of formula I used as starting materials are prepared by acylation of the corresponding 3-hydroxy substituted compound preferably wherein the 4-carboxyl group thereof is protected by a readily removable blocking group, with an appropriate sulfonylating agent e.g. trifluoromethanesulfonic anyhydride, p-toluenesulfonic anhydride or p-nitrobenzenesulfonyl chloride. Where L is a hetercyclicthio group the corresponding compound of Formula I wherein L is one of the said sulfonyloxy groups is allowed to react at low temperature (−78° C. to −20° C.) with the sodium salt of the appropriate mercaptan such as 2-mercaptobenzothiazole or 1-methyltetrazol-5-ylthiol.

The organocuprates employed in the process are prepared according to published methods. e.g. B. H. Lipshutz op. cit., by treating a suitable copper salt such as copper (1) iodide, or copper (1) cyanide with an alkyl lithium (RLi wherein R is as defined with respect to Formula II) at −78° C. in tetrahydrofuran or diethyl ether. They may also be prepared from stannanes as described by A. L. Campbell, et al., U.S. Pat. No.

4.785.124 patented Nov. 15, 1988. In this fashion di-Z-propenylcuprate useful in preparing cefprozil was prepared by treating copper (1) iodide or copper (1) cyanide with methyllithium and tri-n-butyl -(Z)-propenylstannane in tetrahydrofuran. The organocuprates are preferably prepared immediately prior to contact with the cephalosporin starting material of Formula I.

Suitable aprotic reaction inert organic solvents include tetrahydrofuran, which is preferred, and diethyl ether, but others may be employed. The optimum reaction time and temperature for any given set of raw materials can easily be determined by trial and error since the process involves only simple manipulations. Most generally at temperature in the range of $-78°$ C. to $0°$ C. for from 1 to 5 hours will be found suitable.

EXPERIMENTAL PROCEDURES

Procedure 1

Diphenylmethyl 7-Phenoxyacetamido-3-trifluoromethanesulfonyl--oxy)ceph-3-em-4-carboxylate.

This compound was prepared according to the procedure of Baker, et al.. U.S. Pat. No. 4 870.168.

Procedure 2

Diphenylmethyl 7-Phenoxyacetamido-3-(p-toluenesulfonyloxyl)ceph3-em-4-carboxylate.

A solution of diphenylmethyl 7-phenoxyacetamido-3-hydroxy-3-cephem-4-carboxylate (5.0 gm. 9.68 mmol) in 15 ml of dry tetrahydrofuran was cooled to $-78°$ C. To the stirred solution, under an inert atmosphere of nitrogen, was added sodium hydride (0.23 g. 9.68 mmol) followed by p-toluenesulfonic anhydride (2.78 g, 11.6 mmol). The solution was slowly warmed to room temperature and the mixture was stirred for 18 hrs. The reaction mixture was poured into ice-water (25 ml) and the aqueous layer was extracted with ethyl acetate ( $3 \times 20$ ml). The combined organic layer was dried (anhydrous magnesium sulfate), and evaporated in vacuo to give light brown foam which was further purified by recrystallization using 2-propanol; yield-5.80 gm. 90%.

Procedure 3

Diphenylmethyl 7-Phenoxyacetamideo-3-(p-nitrobenzenesulfonyloxyceph-3-em-4-carboxylate.

This compound was prepared according to the method described in Procedure 2. p-Nitrobenzenesulfonyl chloride was employed instead o p-toluenesulfonic anhydride.

Procedure 4

Diphenylmethyl 7-Phenoxyacetamido-3-[5-(1-methyl-1,2,3,4tetrazolythio)]ceph-3-em-4-carboxylate.

To a solution of diphenylmethyl 7-phenoxyacetamido-3-(trifluoromethylsulfonyloxy)-3-cephem-4-carboxylate (1.0 gm, 1.54 mmol) in 15 ml of tetrahydrofuran was added, in portions, 5-mercapto-2-methyl-tetrazole, sodium salt hydrate (0.25 gm, 1.85 mmol). The solution was stirred at room temperature for 12 hours and poured into 10 ml of water. The aqueous layer was extracted with ethyl acetate ($3 \times 5$ ml), dried (anhydrous magnesium sulfate) and evaporated to give the title compound as a dark brown foam which was further purified by flash chromatography (silica, 40% ethyl acetate in hexanes) to give the purified product as a white foam. (Yield $-0.8$ gm, 85%).

($^1$H-NMR-CDCl$_3$) 7.40–7.23 (m, 12H), 7.05–6.86 (m, 4H), 5.98 (dd, J=5.07 and 9.8 Hz, 1H), 5.10 (d, J=5.0 Hz, 1H), 4.55 (S, 2H), 3.81 and 3.40 (ABq, J=18.9 Hz, 2H), 3.78 (s, 3H).

Procedure 5

Diphenylmethyl 7-Phenoxyacetamido-3-(2-benzothiazolylthio)ceph-3-em-4-carboxylate.

To a solution of 2-mercaptobenzothiazole (0.26 g. 1.54 mmol) in dry tetrahydrofuran (5.0 ml) at $-78°$ C. was added sodium hydride (98%) (0.0369 g. 1.54 mmol). followed by diphenylmethyl 7-phenoxyacetamido-3-(trifluoromethylsulfonyloxy)-3-cephem-4-carboxylate (1.0 gm, 1.54 mmol). The reaction was warmed up to $-20°$ C. and stirred for 16 hours before quenching in 0.5 N solution of hydrochloric acid (5 ml). The aqueous layer was extracted with dichloromethane ($3 \times 5$ ml), dried (magnesium sulfate) and evaporated in vacuo to give the title compound as an oil which was purified by flash chromatography (silica, 40% ethylacetate in haxanes); yield isolated 0.7 g (70%).

($^1$H-NMR-CDCl$_3$): 7.85–6.82 (m, 21H), 5.95 (dd, J=5.0 and 9.7 Hz, 1H), 5.15 (d=5.0 Hz, 1H), 4.55 (s, 2H), 3.85 and 3.55 (ABq. J=18.9 Hz, 2H).

Procedure 6

General Alkylation Procedure Using R$_2$CuLi/BF$_3$·Et$_2$O,

Into a two-necked flask, under argon or nitrogen atmosphere, containing copper (1) iodide (1.54 mmol) dry tetrahydrofuran (2.0 ml) was added. The slurry was cooled to $-78°$ C. (dry ice-acetone bath) and to this solution there was added, dropwise with stirring, alkyl-lithium (3.08 mmol). The cooling bath was removed and the mixture was allowed to warm to $-10°$ C. and $0°$ C. until complete dissolution of the copper iodide occurred. The solution was again cooled to $-78°$ C. and boron trifluoride etherate (1.23 mmol) was added followed by the cephem (0.30 mmol, dissolved in 1.0 ml of tetrahydrofuran). The reaction mixture was stirred for 1-5 hours at $-78°$ C. to $0°$ C. before quenching with saturated ammonium chloride (15 ml). The aqueous layer was extracted with dichloromethane ($3 \times 10$ ml). dried (magnesium sulfate) and evaporated to give the product which was further purified by recrystallization or flash chromatography.

Procedure 7

General Procedure Using R$_2$CuLi

Similar to Procedure 6, except boron trifluoride etherate was excluded.

Procedure 8

General Procedure Using R$_2$Cu(CN)Li$_2$/BF$_3$·Et$_2$O.

Into a two necked flask, under a nitrogen or argon atmosphere, was placed cooper cyanide (0.616 mmol) followed by dry tetrahydrofuran (2.0 ml). The slurry was cooled to $-78°$ C. and the alkyllithium (1.23 mmol) was added. With gentle stirring the flask was allowed to warm to $-10°$ C. and $0°$ C. until complete dissolution of the copper cyanide occurred. The solution was again cooled to $-78°$ C. and boron trifluoride etherate (1.23 mmol) was added followed by the cephem (0.30 mmol, dissolved in 1.0 ml of tetrahydrofuran). The reaction mixture was stirred for 1-5 hours at −78° C. to 0° C. before quenching with saturated ammonium chloride (15 ml). The aqueous layer was extracted with dichloromethane (3×10 ml), dried (magnesium sulfate) and evaporated to give the product which was further purified by recrystallization or flash chromatography.

Procedure 9

General Procedure Using $R_2Cu(CN)Li_2$

Similar to Procedure 8, except borontrifluoride etherate was omitted.

Procedure 10

$R_2CuLi$, Lower-order Cuprate From Stannane.

Into a two-necked flask, under an inert atmosphere, was placed copper iodide (1.54 mmol) followed by dry tetrahydrofuran (2.0 ml). The slurry was cooled to −78° C. (dry ice-acetone) and to the stirred solution was added, tributyl-alkenyl-stannane (3.08 mmol) followed by alkyl lithium (3.08 mmol), dropwise, and the solution was stirred for 3.0 hrs at −78° C. The cephem reactant (0.30 mmol, dissolved in 1.0 ml of tetrahydrofuran) was added and the reaction mixture was stirred for additional 1-2 hours at −78° C. to 0° C. before quenching with saturated aqueous ammonium chloride solution (10 ml). The aqueous layer was extracted with dichloromethane (3×10 ml), dried (magnesium sulfate), and evaporated to give the organocopper compound which was purified further by flash chromatography (30-40%) ethyl acetate in hexanes).

Procedure 11

$R_2CU(CN)Li_2$, Higher-order Cuprate From Stannane.

Into a two necked flask, under an inert atmosphere. (nitrogen or argon) was added copper cyanide (0.27 mmol) followed by tetrahydrofuran (2.0 ml). The solution was cooled to −78° C. (dry ice-acetone) and methyl lithium (0.76 mmol) was added dropwise. The ice bath was removed and the mixture was allowed to warm up (−10° C.) before adding tributyl-alkenyl-stannane (0.76 mmol). The clear solution was stirred at room temperature for 3.5 hours. The solution was cooled to −78° C. and a solution of the cephem (0.38 mmol) in tetrahydrofuran (1.5 ml) was added. The reaction was stirred for 1-2hours between −78° to 20° C. before quenching with saturated ammonium chloride (10 ml). The aqueous layer was extracted with methylene chloride (3×10 ml), dried (magnesium sulfate). and evaporated to give the crude product which was purified by chromatography (silica, 30-40% ethyl acetate in hexanes.

In each of the following Procedures the product produced was characterized and identified by examination of the nuclear magnetic resonance spectrum.

Procedures 12-18

Preparation of Diphenylmethyl 7-Phenoxyacetamido-3-methylceph-3-em-4-carboxylate.

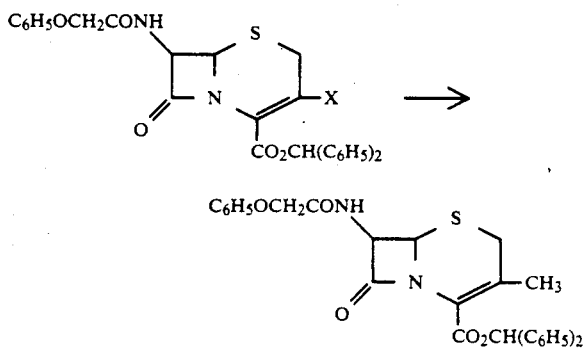

12. $X = -OSO_2CF_3$
$(CH_3)_2$ CuLi/$BF_3 \cdot Et_2O$ according to Procedure 6.

Yield 65%

13. $X = -OSO_2CF_3$
$(CH_3)_2$ CuLi according to Procedure 7.

Yield 65% of a 1:1 mixture of the ceph-2-em and the ceph-3em.

14. $X = -OSO_2CF_3$
$(CH_3)_2Cu(CN)Li_2$/$BF_3 \cdot Et_2O$ according to Procedure 8.

Yield 85%

15. $X = -OSO_2CF_3$
$(CH_3)_2Cu(CN)Li_2$ according to Procedure 9.

Yield 65% of a 3:2 mixture of ceph-3-em and ceph-2-em product.

16. $X = -OSO_2C_6H_4CH_3-p$
$(CH_3)_2$ CuLi/$BF_3 \cdot Et_2O$ according to Procedure 6.
Yield 62%

17. $X = -OSO_2C_6H_4NO_2$-p
$(CH_3)$ CuLi/$BF_3 \cdot Et_2O$ according to Procedure 6.
Yield 35%

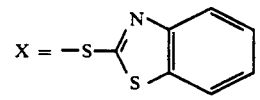

$(CH_3)_2CuLi$/$BF_3 \cdot Et_2O$ according to Procedure 6.
Yield 45%

Procedures 19-20

Preparation of p-Methoxybenzyl 7-Phenylacetamido-3-methylceph-3-em-4-carboxylate.

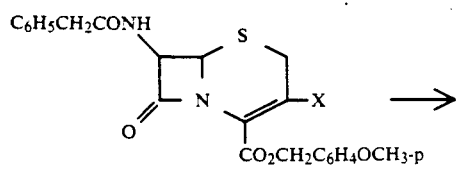

-continued

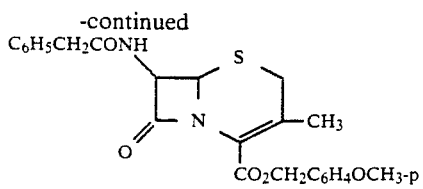

19. X=—OSO₂CF₃
$(CH_3)_2$ CuLi/BF₃·Et₂O according to Procedure 6. Yield 75%

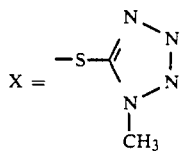

$(CH_3)_2$ CuLi/BF₃·Et₂O according to Procedure 6. Yield 81%

Procedure 21

Diphenylmethyl 7-Phenoxyacetamido-3-ethylceph-3-em-4-carboxylate.

The product of Procedure 1 was treated with $(C_2H_5)_2$ CuLi/BF₃·Et₂O according to the method of Procedure 6, yield 75%.

Procedure 22

Diphenylmethyl 7-Phenoxyacetamido-3-(n-butyl)ceph-3-em-4-carboxylate.

The product of Procedure 1 is allowed to react with $(n-C_4H_9)_2$ CuLi/BF₃·Et₂O according to the method of Procedure 6. yield 60%.

Procedure 23

Diphenylmethyl 7-Phenoxyacetamido-3-(tert.-butyl)-ceph-3-em-4-carboxylate.

The product of Procedure 1 was treated with (tert.-butyl)₂ CuLi/BF₃·Et₂O according to the method of Procedure 6; yield 70%.

($^1$H-NMR-CDCl₃): 7.40–7.20 (m, 15H), 7.02 (s, 1H), 6.90 (d, J=9.5Hz), 5.83 (dd. J=4.75 and 9.5 Hz,1H), 4.95 (d, J=4.75 Hz, 1H), 4.53 (s, 2H). 3.45 and 3.30 (ABq. 2H, J=18.9 Hz), 1.05 (s, 9H).

Procedure 24

Diphenylmethyl 7-Phenoxyacetamido-3-phenylceph-3-em-4carboxylate

The product of Procedure 1 was treated with $(C_6H_5)_2$ CuLi/BF₃·Et₂O according to the method of Procedure 6; yield 65%

($^1$H-NMR-CDCl₃): 7.36–6.81 (m, 22H), 5.96 (dd, J=5.0 and 9.8 Hz, 1H), 5.10 (d, J=5.0 Hz, 1H), 4.58 (S, 2H). 3.62 (S, 2H).

Procedure 25

Diphenylmethyl 7-Phenoxyacetamido-3-vinyl-ceph-3-em-4-carboxylate

The product of Procedure 1 is treated with $(CH_2=CH)_2CuLi/BF_3\cdot Et_2O$ according to the method of Procedure 6, yield 35%.

($^1$H-NMR-CDCl₃): 7.44–6.83 (m, 18H), 5.92 (dd, J=4.87 and 9.30 Hz, 1H), 5.41 (d, J=17.2 Hz, 1H), 5.26 (d, J=11.2 Hz, 1H), 5.05 )d, J=4.87 Hz, 1H), 4.55 (s, 2H), 3.62 and 3.47 (ABq, J=17.8 Hz. 2H).

Procedure 26

Diphenylmethyl 7-Phenoxyacetamido-3-((Z)-prop-1-en-1-yl)ceph-3-em-4-carboxylate (a) The product of Procedure 1 was allowed to react with (Z-prop-1-en-1-yl)z CuLi/BF₃·Et₂O according to Procedure 10, yield 26%.

(b) The product of Procedure 1 was allowed to react with (Z-prop-1-en-1-yl)CH₃Cu(CN)Li₂ according to Procedure 11 modified by the use of 0.63 mmole of tributyl (Z-prop-1-en-1-yl)stannane; yield 60% of a 2:3 mixture of the ceph-3-em and the ceph-2-em.

(c) The product of Procedure 2 is allowed to react with (Z-prop-1-en-1-yl)₂ CuLi/BF₃·Et₂O according to the method of Procedure 10: yield 31% of a mixture ceph-3-em and ceph-2-em compounds.

(d) The product of Procedure 2 is allowed to react with (Z-prop-1-en-1-yl) CH₃Cu(CN)Li₂ according to the method of Procedure 11 modified by the use of 0.60 mmole of tributyl (Z-prop-1-enyl)stannane to yield 59% of the product as 2:3 mixture of ceph-2em and ceph-3-em.

(e) Reaction of (Z-prop-1-en-1-yl)₂CU(CN)Li₂ with the product of Procedure 2 according to the method of Procedure 11 yields 60% of the product as a 2.3 mixture of ceph-2-em-and ceph3-em.

($^1$H-NMR-CDCl₃) Diphenylmethyl 7-phenoxyacetamido-3-(Z-propenyl)-3-cephem-4-carboxylate (14). 7.51–6.90 (m. 17H). 6.10 (d, J=11.7 Hz, 1H), 5.90 (dd, J=4.5 and 9.8 Hz, 1H), 5.56 (m, 1H), 5.07 (d, J=4.5 Hz, 1H), 4.58 (s, 2H), 3.47 and 3.27 (ABq, J=17.5 Hz, 2H), 1.43 (d, J=7.0 Hz,3H).

($^1$H-NMR-CDCl₃) Diphenylmethyl 7-phenoxyacetamido-3-(Z-propenyl)-2-cepehm-4-carboxylate (14A) 7.51–6.90 (m. 17H, 6.10 (s, 1H), 5.71 (m, 2H), 5.56 (m, 1H), 5.33 (d, J-4.05 Hz, 1HO, 4.92 (s, 1H), 4.58 (s, 2H), 1.62 (d, J=7.0 Hz, 3H).

What is claimed is:

1. The process for preparing a cephalosporin having the formula

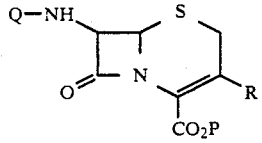

wherein

Q is hydrogen, an amine protecting group conventionally used in cephalosporin synthesis, or the acyl group of a known 7-acylaminocephalosporin antibiotic;

P is hydrogen, a carboxy protecting group conventionally used in cephalosporin synthesis, a cation, or a physiologically hydrolyzable ester group; and R is selected from the group consisting of $C_{1-6}$ alkyl, $C_{2-6}$ alkenyl, $C_{2-6}$alkynyl, $C_{4-6}$alkadienyl, $C_{6-10}$aryl, substituted $C_{6-10}$aryl, wherein said substituted aryl bears 1 to 3 groups selected from $C_{1-3}$alkyl, hydroxy, $C_{1-3}$alkoxy, halo, amino, $C_{1-3}$alkylamino, di$C_{1-3}$alkylamino, nitro, carboxyl, $C_{1-3}$alkoxycarbonyl, or cyano; said process comprises reacting a compound of formula

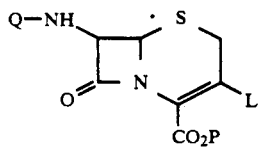

wherein Q and P are as defined above, and L is selected from the group consisting of trifluoromethanesulfonyloxy, p-toluenesulfonyloxy, 4-nitrobenzenesulfonyloxy, 1-methyltetrazol-5-ylthio, and benzthiazol-2-ylthio, and an organocopper reagent of the formula $R_2CuLi$, or $R_2Cu(CN)Li_2$ at a temperature in the range of $-78°$ C. to $0°$ C. in an inert solvent.

2. The process of claim 1 wherein said reaction is carried out in the presence of an equimolar proportion of boron trifluoride etherate relative to said organocopper reagent.

3. The process of claim 1 wherein R is $C_{1-6}$ alkyl.

4. The process of claim 1 wherein R is methyl.

5. The process of claim 1 wherein R is $C_{2-6}$ alkenyl.

6. The process of claim 1 or 2 wherein R is (Z)-1-propenyl.

7. The process of claim 1 wherein L is trifluoromethanesulfonyloxy.

8. The process of claim 1 wherein L is 4-nitrobenzenesulfonyloxy.

9. The process of claim 1 wherein L is p-toluenesulfonyloxy.

10. The process of claim 1 wherein said organocopper reagent has the formula $R_2CULi$.

11. The process of claim 1 wherein said organocopper reagent has the formula $R_2Cu(CN)Li_2$.

* * * * *